United States Patent [19]

Hashimoto et al.

[11] Patent Number: 5,080,495

[45] Date of Patent: Jan. 14, 1992

[54] METHOD AND APPARATUS FOR MEASURING THERMAL DIFFUSIVITY BY AC JOULE-HEATING

[75] Inventors: Toshimasa Hashimoto, Tokyo; Akira Miyamoto, Zushi; Kohei Shizuka; Teruo Hyugaji, both of Yokohama, all of Japan

[73] Assignee: Mitsui Toatsu Chemicals, Inc., Tokyo, Japan

[21] Appl. No.: 573,810

[22] Filed: Aug. 28, 1990

[51] Int. Cl.⁵ .............................. G01N 25/20
[52] U.S. Cl. .............................. 374/43; 374/119
[58] Field of Search ........... 374/43, 44, 120, 119 X, 374/117

[56] References Cited

U.S. PATENT DOCUMENTS

| | | | |
|---|---|---|---|
| 3,533,273 | 10/1970 | Green | 374/43 |
| 3,538,750 | 11/1970 | Lynnworth | 374/119 |
| 3,570,302 | 3/1971 | Sauer | 374/43 |
| 3,611,786 | 10/1971 | Schorr | 374/44 |
| 3,662,587 | 5/1972 | Allen et al. | 374/44 |
| 4,236,403 | 12/1980 | Poppendiek | 374/44 |
| 4,630,938 | 12/1986 | Piórkowska-Palczewska | 374/43 |
| 4,859,078 | 8/1989 | Bowman et al. | 374/44 |

FOREIGN PATENT DOCUMENTS

| | | | |
|---|---|---|---|
| 2324109 | 11/1974 | Fed. Rep. of Germany | 374/43 |
| 0218955 | 2/1985 | Fed. Rep. of Germany | 374/44 |
| 0036944 | 2/1985 | Japan | 374/44 |
| 0161140 | 6/1989 | Japan | 374/44 |
| 0173988 | 8/1965 | U.S.S.R. | 374/43 |
| 0306406 | 6/1971 | U.S.S.R. | 374/43 |
| 0838538 | 6/1981 | U.S.S.R. | 374/44 |
| 0894512 | 12/1981 | U.S.S.R. | 374/44 |
| 1057828 | 11/1983 | U.S.S.R. | 374/44 |
| 1293606 | 2/1987 | U.S.S.R. | 374/44 |

*Primary Examiner*—William A. Cuchlinski, Jr.
*Assistant Examiner*—G. Bradley Bennett
*Attorney, Agent, or Firm*—Burns, Doane, Swecker & Mathis

[57] ABSTRACT

Disclosed is a method for measuring the thermal diffusivity in the thickness direction of a thin sample plate, which has the steps of forming a conductive thin layer on at least one surface of said thin sample plate to allow the thin film to function as an ac heater generating joule heat, applying an ac current modulated with a given modulation frequency to the ac heater (conductive thin layer) so as to produce ac joule-heating, generating an oscillation response corresponding to said ac joule-heating on the opposite surface of the ac heater, and measuring the phase shift between said oscillation response, and the ac joule-heating, thereby obtaining the thermal diffusivity in the thickness direction of said sample plate. Apparatus useful for the method are also disclosed.

32 Claims, 5 Drawing Sheets

THERMAL DIFFUSIVITY

METHOD AND APPARATUS FOR MEASURING THERMAL DIFFUSIVITY BY AC JOULE-HEATING

BACKGROUND OF THE INVENTION (i) Field of the Invention

This invention relates to a method for measuring thermal diffusivity of material, an apparatus used for this purpose, and a method for measuring thermal conductivity. Particularly, it relates to a measuring method and apparatus depending on the non-steady state method (where the temperature is not kept constant and hence is allowed to vary) for precise measurements of the thermal diffusivity of a hardly conductive material such as high molecular compounds (polymers) and ceramics, and to a method for measuring its thermal conductivity by the use of the measured value of the thermal diffusivity obtained according to the method for measuring thermal diffusivity.

(ii) Description of the Background Art

Thermal diffusivity and thermal conductivity are among important properties for determining the processing and use conditions of a variety of materials including high molecular compounds (polymers) upon their material and product designs. Recently, a number of various simulation programs have been developed keeping pace with the advance of computerization, and material and product designs making use of these programs have been put into practice so often. For instance, structural analysis for analyzing the stress or deformation of processed products or structures and thermal conduction analysis for analyzing heat transfer phenomena have already been applied widely. Heat flow analysis for analyzing the behavior of resins in a mold in the injection molding has recently been utilized in many cases. The analytical accuracy of these simulation programs is largely dependent on the accuracy of the physical property values used in the analyses, not to mention the contents of the programs. Accordingly, in order to improve their analytical accuracy and perform precise material and product designs, it has been desired to measure the physical properties of the object material with high precision.

Processed products are often used practically not only at room temperature but also at high temperatures. While processing, most of high molecular materials undergo a molding process in which they are molten at high temperatures and then cooled to room temperature. Therefore, when material and product designs are carried out taking into account the actual use and processing conditions of a product or when analysis is conducted on the basis of actual phenomena, it is necessary to know its physical properties in the wide range of temperature from room temperature to the melting temperature or above.

Lately, it has frequently been practiced to use processing materials in a composite form, so that their combinations have become diversified and complicated. On measuring physical properties for the material development and design of such a particular processing material, it has often been difficult to obtain a large amount of its sample. It has also become necessary to know its physical properties as quickly as possible and reflect the results without delay in the development and design of its product. As a result, rapid measurement of the physical properties has been demanded with a small amount of sample.

The method for measuring thermal diffusivity is broadly divided into the steady state method and the non-steady state method. The method for measuring thermal diffusivity according to the non-steady state method is characterized in that the thermal diffusivity is determined by producing forcibly a thermally non-equilibrium state in a sample and measuring the temperature variation of the sample caused by the subsequent relaxation of the state. Thus, the method has such an advantage over the steady state method that measuring time is significantly reduced.

Typical methods for measuring thermal diffusivity according to the conventional non-steady state method include the Angstrom method, the flash method and the PAS method. The Angstrom method calculates thermal diffusivity in the following manner: A portion of a rod sample, which has a sufficiently small cross sectional area relative to the length, is brought into contact with a heat source which causes periodical heating and cooling, whereby a periodic temperature variation is produced on the end of the sample and, in consequence, a temperature wave is brought about in the sample. The state of propagating the temperature wave in the sample is observed by measuring the temperature at not less than two measuring points which are different in distance from the heating point in the propagation direction of the wave. Using the amplitude and phase of the temperature wave obtained at each measuring point, the thermal diffusivity is calculated.

The flash method measures thermal diffusivity in the following manner: One of the surfaces of a plate sample is provided with a light absorption layer, to which a laser pulse, for example, is irradiated to effect instantaneous heating through light absorption. The temperature rise thereby caused at the absorption layer is propagated in the thickness direction of the sample so that a temperature variation is produced on the surface of the sample opposite to the irradiated surface. The temperature variation is measured as a function of time after the flash irradiation. From the temperature-time curve thus obtained, the thermal diffusivity is determined.

The PAS method determines thermal diffusivity in the following manner: A closed cell having a window for transmitting light is equipped with a microphone, etc. for measuring sound signal. A plate sample within the cell is provided with a light absorption layer at one surface thereof. A modulated light beam is irradiated through the window to the layer to produce a periodic temperature variation. This temperature wave is propagated to cause a periodic temperature variation on the opposite surface of the sample. Then, the variation of a periodic sound wave thereby generated in the cell is measured. Using the phase and amplitude of the wave, the thermal diffusivity is determined.

The conventional measuring methods described above involve the following problems.

In the Angstrom method, since the sample has to be molded into a long rod, a great amount of sample material is required, and the installation of its adiabatic system becomes large in order to minimize the heat loss from the surface of the sample. Further, the measurement requires a relatively long time and hence the objects to be measured are limited to materials of relatively large thermal diffusivities.

Since the flash method effects heating through light absorption, when a transparent sample or a sample of little light absorption is measured, it is necessary to coat an absorption layer for light absorption on the surface of the sample. This often causes a heat loss or heating irregularity at the interface of the absorption layer and the sample, which are responsible for errors. Further, the measurement is carried out on the assumption that no consideration of heat loss may be made because of short time. This assumption is well met by those with large thermal diffusivities such as metals. However, with those of smaller thermal diffusivities such as high molecular compounds, large errors will result.

In the PAS method, the same problems as in the flash method arise owing to the heating through light absorption. Further, since the method measures sound signal by means of a sound signal detector, it is affected seriously by noises caused by vibration, sound, etc.

Moreover, it is difficult for these measuring methods to measure the temperature-dependence of thermal conductivity. This measurement in actual practice necessitates an elaborate apparatus.

It is the objects of the present invention to solve the foregoing problems, and to provide a method for measuring thermal diffusivity, according to which precise measurements can be made even with materials of small thermal diffusivities, measurements can be made with trace amounts of samples, and rapid measurements including the temperature-dependence can be made in a small scale apparatus, an apparatus thereof, and a method for measuring thermal conductivity according to which the thermal conductivity is determined from the measured value of the thermal diffusivity.

SUMMARY OF THE INVENTION

According to the present invention, there is provided a method for measuring the thermal diffusivity in the thickness direction of a thin sample plate which comprises the steps of forming a conductive thin layer on at least one surface of said thin sample plate to allow the thin layer to function as an ac heater generating joule heat, applying an ac current modulated with a given modulation frequency to the ac heater of said sample plate so as to produce ac joule-heating, generating an oscillation response corresponding to said ac joule-heating on the opposite surface of said sample plate, and measuring the phase shift of said oscillation response, thereby obtaining the thermal diffusivity in the thickness direction of said sample plate.

DETAILED DESCRIPTION OF THE INVENTION

The present invention will be described in detail hereunder.

The sample to be measured (hereinafter referred to as measurement sample) in the present invention is of hardly conductive materials which can be formed into thin films, sheets or plates. They may include, for example, I. high molecular compounds (polymers) such as phenol, urea, melamine, polyester, epoxy, polyurethane, cellulose, polystyrene, polypropylene, polyethylene, vinylidene chloride, polyamide, polyacetal, polycarbonate, polysulfone, ABS, polyphenylene oxide, polyether sulfone, polyallylate, acryl, acrylonitrile, polyether ether ketone, polyether ketone, polyimide and polyolefin, II. organic dyestuffs such as cyanine, phthalocyanine, naphthalocyanine, nickel complex, spiro-compounds, ferrocene, fulgide, imidazole, perillene, phenazine, phenothiazine, polyene, azo-compounds, quinone, indigo, diphenylmethane, triphenylmethane, polymethine, acridine, acridinone, carbostyril, coumarin, diphenylamine, quinacridone, quinophthalone, phenoxazine and phthaloperinone, III. mineral ores such as silica, diamond, garnet, corundum, ruby, sapphire, agate, zeolite, diatomaceous earth, mica, rock salt, apatite, kaolin, sillimanite, andalusite, cyanite, dolomite, moonstone, marble, serpentine, malachite, bauxite, bentonite, quartz, olivine, gypsum, sulfur, barite, alunite, fluorite, feldspar, talc, asbestos, limestone, calcite, crystal, amber, spinel, alexandrite, emerald, topaz, cat's-eye, jade and opal, IV. glasses such as quartz glass, fluoride glass, soda glass, soda lime glass, barium-strontium glass, lead glass, aluminoborosilicate glass, borosilicate glass, aluminosilicate glass and silica glass, and V. fine ceramics such as $Al_2O_3$, $MgAl_2O_4$, BeO, SiC, AlN, MgO, PLZT, $Y_2O_3$, $ZrO_2$, $TiO_2$, $CaF_2$, GaAs, PbO, CaO, $La_2O_3$, $Si_3N_4$, a-Si:H, etc.

The thickness is so thin that the thermal diffusion can be ignored in the surface direction and hence is regarded as being completely adiabatic in the surface direction.

The conductive materials to be used as the ac heater (electrically conductive thin layer) generate joule heat by passing a current therethrough. They may, for example, include gold, silver, platinum, copper, iron zinc, antimony, iridium, chromel, constantan, nichrome, aluminum, chromium, nickel and carbon.

The conductive materials to be used as the resistance thermometer (discussed later) are those whose resistance varies with temperature. They may, for example, include gold, silver, platinum, copper, iron, zinc, antimony, iridium, chromel, constantan, nichrome, aluminum, chromium, nickel and carbon.

The conductive thin layer to be used as the ac heater and the resistance thermometer should be thin enough in thickness and small enough in heat capacity compared with the sample plate to such an extent that their contacting interfaces with the sample plate can be ignored.

The conductive thin layers used as the ac heater and resistance thermometer are formed on the sample plate intimately by I. sputtering which forms a thin layer by allowing the sample plate to adsorb atoms at its surface, making use of the phenomenon that irradiation of ions onto the surface of a solid liberates the atoms of the solid, II. vapor deposition which forms a thin layer by allowing the sample plate to adsorb the vapor of a substance at its surface under vacuum, III. coating which coats the surface of the sample plate with a liquid or semi-liquid material, IV. adhesion which sticks the surfaces together with the help of an adhesive comprising the same or different material, or V. pressure application which sticks the surfaces together by an application of pressure without using any adhesive comprising the same or different material.

Among these, sputtering or vapor deposition is most preferred.

When, by way of example, gold is used to form a conductive thin layer on a sample plate by sputtering, it is preferred that the sample plate is first masked with a polyester film, etc., and then allowed to adsorb (deposit) gold for about 30 minutes under vacuum by the use of a voltage and current of around 1.2 KV and 3.5 mA, respectively, to form a conductive thin layer of a thickness of around 10–5,000 angstroms and a resistance of around 0.1Ω–10 KΩ.

When gold is used by way of example to form a conductive thin layer on a sample plate by vapor deposition, it is preferred that the sample plate is first masked with a polyester film, etc. and then allowed to adsorb (deposit) gold for 30 minutes by vaporizing gold by heating it electrically under vacuum to its melting temperature or above to form a conductive thin layer of a thickness of around 10–5,000 angstroms and a resistance of around 0.1Ω–10 KΩ.

When a sample plate and a conductive thin layer are formed by coating, it is preferable to coat the sample plate with a conductive paste so as to form a layer of a thickness of around 10–5,000 angstroms and a resistance of around 0.1Ω–10 KΩ.

When a measurement sample plate and a conductive thin film are stuck together by adhesion, it is preferable first to coat a conductive thin film, such as copper leaf or gold leaf, etc. of a thickness of around 10–5,000 angstroms and a resistance of 0.1Ω–10 KΩ, with an adhesive so thin that the contacting interface between the conductive thin film and the sample plate can be ignored, and then to allow the film with adhesive to adhere to the sample plate so completely that they are not peeled off each other.

When a sample plate and a conductive thin film are joined together by pressure application, it is preferable to press a conductive thin film, such as copper leaf or gold leaf, of a thickness of 10–5,000 angstroms and a resistance of 0.1Ω–10 KΩ onto the sample plate with a force higher than the pressure, under which the effect of the contacting interface between the conductive thin film and the sample plate can be ignored, so as to allow them to adhere to each other completely.

The basic composition of the present invention and the features thereof will be illustrated hereunder with reference to the attached drawings.

Figure 1:
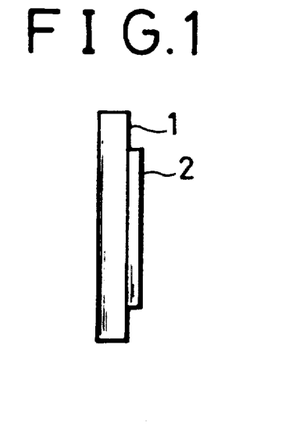
FIGS. 1 and 1' are individually a side-view illustrating the structure of a measurement sample plate in the present invention.

In FIGS. 1 and 1', numeral 1 is a measurement sample plate, the thickness of which is substantially uniform and is so thin that the thermal diffusion in the surface direction can be ignored. For example, where the portion for measuring the thermal diffusivity of the sample plate is a square, it is a film or sheet or plate having a ratio (1/d) of the length (1) of a side to the thickness (d) of 10 or more, preferably 50 or more, more preferably 100 or more, the upper limit L of the thickness (d) being not more than 2,000 μm, preferably not more than 1,500 μm more preferably not more than 1,000 μm, the lower limit of the thickness (d) being in such a range that the heat capacities of the conductive thin layers formed on the both surfaces can be neglected, i.e., not less than 0.01 μm, preferably not less then 0.1 μm, more preferably not less than 1 μm. Further, the measurement sample plate 1 is of a hardly conductive material such as high molecular compounds (polymers) and ceramics, the resistivity of which is not less than $1 \times 10^4$ Ω.cm, preferably not less than $1 \times 10^6$ Ω.cm, more preferably not less than $1 \times 17^7$ Ω.cm and has no upper limit but is, for example, not more than $1 \times 10^{21}$ Ω.cm, preferably not more than $1 \times 10^{22}$ Ω.cm, more preferably not more than $1 \times 10^{23}$ Ω.cm. Numeral 2 represents a conductive thin layer functioning as the ac heater for causing ac joule-heating on one surface of the measurement sample plate by a modulated current, the resistance of which is 0.01Ω–100 KΩ, preferably 0.05Ω–50 KΩ, more preferably 0.1ψ–10 KΩ. The conductive thin layer functioning as the ac heater is completely adhered to the sample plate to such an extent that the contacting interface between the sample plate and the ac heater (conductive thin layer 2) can be ignored, the thickness thereof being far thinner than that of the sample plate, e.g., not more than 50,000 angstroms, preferably not more than 10,000 angstroms, more preferably not more than 50,000 angstroms, the lower limit of the thickness being, e.g., not less than 1 angstrom, preferably not less than 5 angstroms, more preferably not less than 10 angstroms, although there is no restriction on the lower limit so far as the layer can pass ac current.

Numeral 3 is a conductive thin layer functioning as the resistance thermometer to measure the ac component of the temperature oscillation response on the surface opposite to the ac heater, the resistance of which is 0.01Ω–100 KΩ, preferably 0.05Ω–50 KΩ, more preferably 0.1Ω–10 KΩ. The conductive thin layer functioning as the resistance thermometer is completely adhered to the sample plate to such an extent that the contacting interface between the sample plate and the resistance thermometer can be ignored, the thickness thereof being far thinner than that of the sample plate, e.g., not more than 10,000 angstroms, preferably not more than 5,000 angstroms, more preferably not more than 1,000 angstroms, the lower limit of the thickness being, e.g., not less than 1 angstrom, preferably not less than 5 angstroms, more preferably not less than 10 angstroms, although there is no restriction on the lower limit so far as the film can pass dc current enough to read the variation of the resistance.

Figure 2:
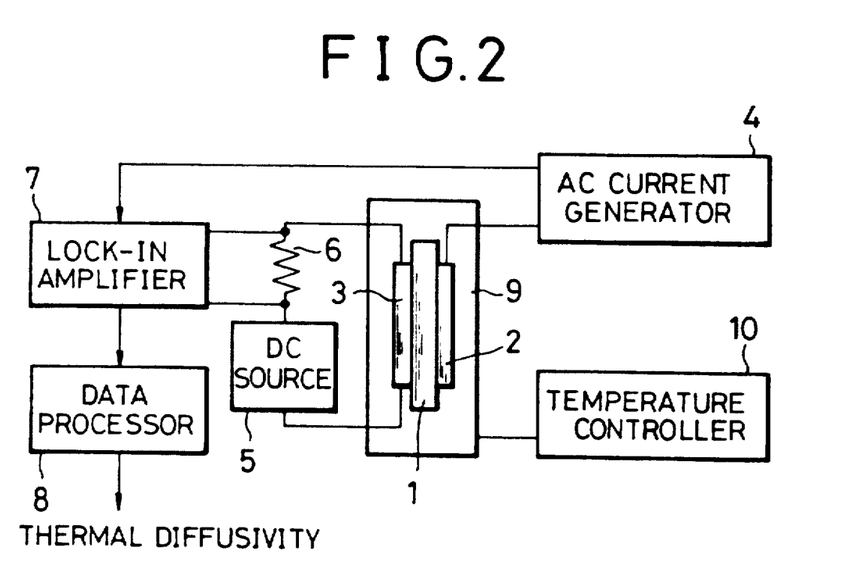
FIGS. 2, 3 and 8 are individually an exemplary schematic diagram of the measuring method and apparatus of the present invention.
Figure 3:
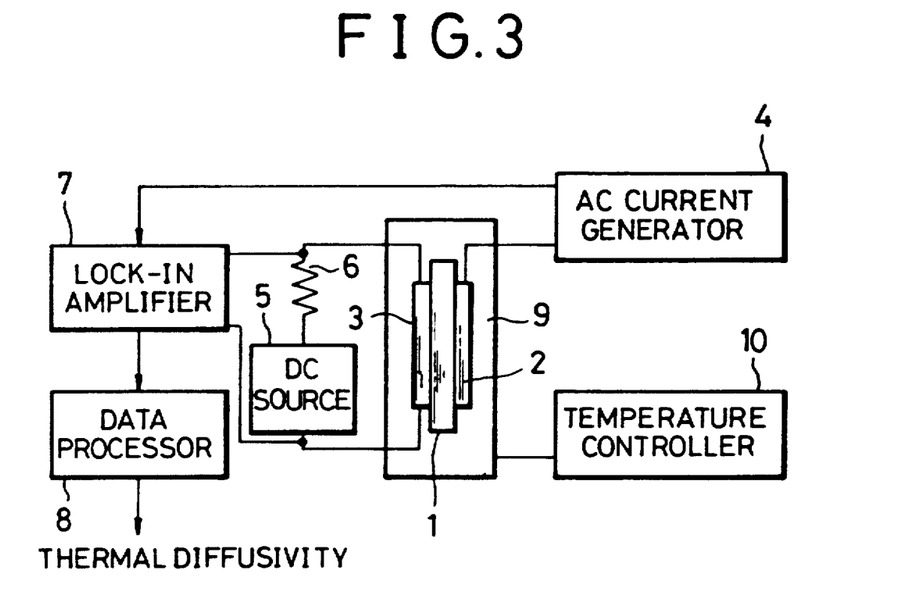
Figure 8:
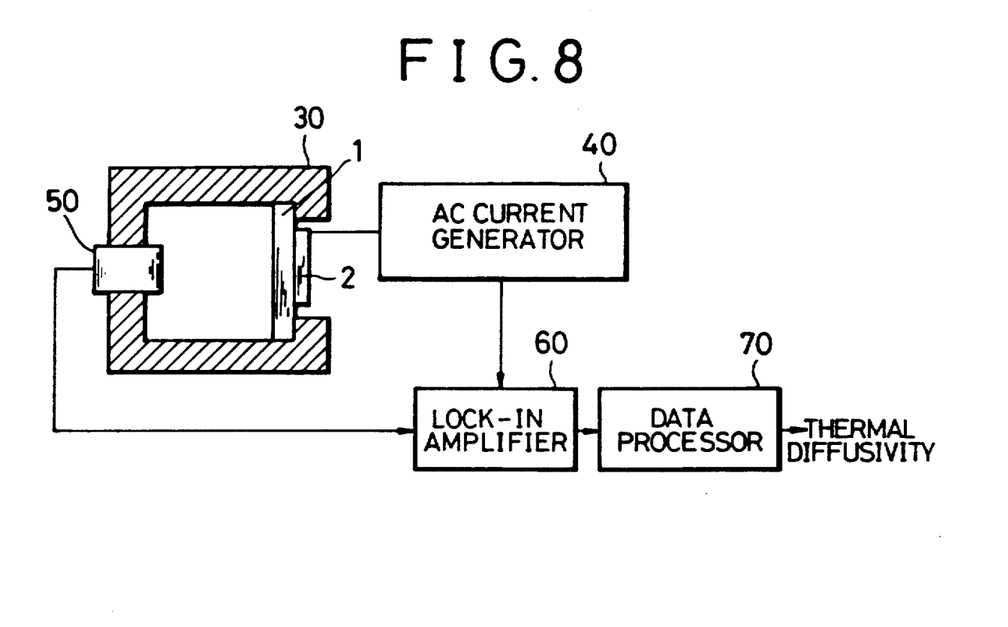

FIGS. 2, 3 and 8 are exemplary schematic diagrams of the measuring method and apparatus of the present invention. FIGS. 2 and 3 illustrates examples in which temperature oscillation response is used as the oscillation response, while FIG. 8 is an example in which periodic sound wave is used as the oscillation response. The examples using the former (temperature oscillation response) is first illustrated.

As shown in FIGS. 2 and 3, an ac current is applied to an ac heater 2 by means of a generator 4 of a modulated ac current (function synthesizer, etc.) so that the ac heater 2 is ac-joule heated. To a resistance thermometer 3, a dc current of a fixed voltage is applied by means of a dc source 5 (battery, etc.), and the variation of the voltage due to the temperature-dependence of the resistance is amplified by a lock-in amplifier 7 to measure the ac component of the temperature oscillation. The lock-in amplifier 7 is incorporated in parallel with a resistance 6, installed for the purpose of preventing self heating of the resistance thermometer, as in FIG. 2, or it is incorporated in parallel with the resistance thermometer as in FIG. 3, so as to measure the ac component of the temperature oscillation response.

The lock-in amplifier 7 obtains a dc component (part) from the product of the reference ac current from the generator 4 of ac current and the detected wave. It has a selectivity so that noises other than necessary frequencies are almost completely eliminated.

The output signals of the lock-in amplifier 7 are sent to a data processor 8 (e.g., personal computer) to determine the thermal diffusivity. The calculation of the thermal diffusivity is effected as follows.

Since the joule heat is maximized at the peak point regardless of the current being positive or negative, the cycle of the temperature oscillation is twice the cycle of the ac current. Accordingly, the ac component (part) of the temperature of the ac heater 2 varies with a frequency f, assuming that the frequency of the modulated ac current is f/2. The varied temperature is expressed as $$T(t) = T_0 \cos(\omega t) \tag{1}$$

taking angular frequency as $\omega(=2\pi f)$.

The sample 1 is of a hardly conductive material, but due to its extremely thin thickness, the heat energy from the joule-heat of the ac heater 2 is transmitted only by thermal conduction in the thickness direction, causing a periodic temperature oscillation response at the resistance thermometer 3 on the opposite surface.

Taking the thickness of the measurement sample plate as d and the thermal diffusivity as $a$, the varied temperature is $$T(t) = T_0 \exp(-\sqrt{\omega/2ad})\cos(\omega t - \sqrt{\omega/2ad}), \tag{2}$$

and noting only the phase shift between the both, it is $$\Delta\theta = \sqrt{\omega/2ad} + \beta \tag{3}$$

Here, $\Delta\theta$ is the phase shift due to the thermal diffusion in the measurement sample plate and $\beta$ is an apparatus constant.

By introducing $\omega = 2\pi f$ in equation (3) followed by modification, $$\Delta\theta = d\sqrt{\pi/a}\,\sqrt{f} + \beta \tag{4}$$

is obtained.

Therefore, with regard to a measurement sample plate having a known thickness d, the thermal diffusivity $a$ can be obtained from equation (4) by causing the modulation frequency to vary at least two points, measuring the phase shift $\Delta\theta$ between the ac heater and the ac component of the temperature measured by the resistance thermometer, and determining the rate of change (gradient, or inclination when expressed as a graph) of the phase shift to the square root of the modulation frequency f.

The lower limit of the frequency range suitable for this measurement is the frequency at which the thermal diffusion length ($\mu_s = \sqrt{2a/\omega}$) is not more than the thickness d of the measurement sample plate, and the upper limit is in such a frequency that the temperature oscillation amplitude measured by the resistance thermometer is larger than noises. The frequency range hence being 0.01 to 1,000 Hz, preferably 0.5 to 700 Hz, more preferably 0.1 to 500 Hz where the measurement sample plate is a high molecular film having a thickness of about 100 μm.

The measurement sample plate 1 is installed in a heating-cooling cell 9, and the measurement atmosphere temperature of the measuring part is regulated by a temperature controller 10. By changing the measurement atmosphere temperature, the temperature dependence of the thermal diffusivity can be measured at any desired temperatures.

Figure 4:
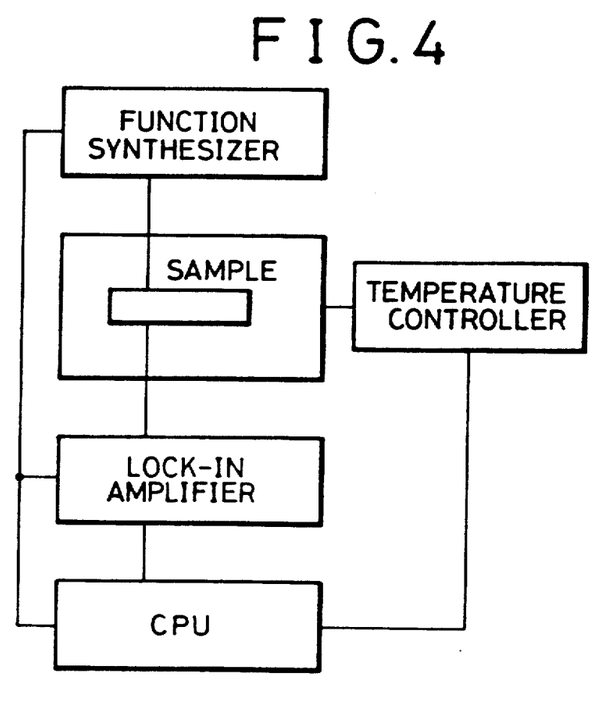
FIG. 4 shows a schematic diagram of an example in which the measuring apparatus of the present invention is automated.

As shown in FIG. 4, these devices are all controlled by a personal computer and the measurements are also treated automatically, constituting an integrated automatic measuring system. By determining the range of measuring frequencies at the beginning of measurement, the output frequency of a function synthesizer, the generator of ac current, is automatically changed after completion of the measurement at each frequency. The measured value by the lock-in amplifier is sent to the personal computer every time the measurement at each frequency is finished, and after completion of measurements in the predetermined range of measuring frequencies, these measured values are stored in a floppy disk. By determining measuring temperatures at the begining of measurement, the temperature is raised or lowered to the next temperature after completion of the measurement at each temperature, and the measurement is repeated automatically until all of the measurements at the predetermined temperatures are completed.

Taking thermal conductivity as $\lambda$, specific heat as Cp and density as $\rho$, the relationship between the thermal diffusivity and the thermal conductivity is expressed as $$a = \lambda/(Cp\cdot\rho) \tag{5}$$

and by modification, as $$\lambda = a \cdot Cp \cdot \rho \tag{6}$$

Thus, the thermal conductivity can be obtained by introducing the values of the specific heat and density measured by other measuring methods in combination with the value of the thermal diffusivity according to the present invention into equation (6). The specific heat can be measured by a differential scanning calorimeter, adiabatic calorimeter, etc., while the density by a volume dilatometer, P-V-T measuring instrument, etc. These measured values are used for obtaining the thermal conductivity.

Hence, making use of the phenomenon that the phase shift of the temperature oscillations between the heating surface by ac heating and the opposite surface thereof depend on the modulation frequency of the ac current flowing through the heating surface, the present invention determines the thermal diffusivity by forming minute conductive thin layers on a minute measurement sample plate, causing one of the thin layers to generate heat by an ac current, and measuring the temperature oscillation on the opposite surface electrically. Since the minute conductive layers are merely formed on the minute measurement sample plate, it is easy to heat or cool the measuring environment uniformly. Thus, the temperature dependence of the thermal diffusivity can be measured by changing the measurement atmosphere temperature at will.

Further, the thermal conductivity can be determined by using measured values of the specific heat and density determined according to other methods.

Then, an example of using the latter periodic sound wave is illustrated.

As shown in FIG. 8, a measurement sample is installed in a sealed cell 30 air-tightly in such a way that the surface to be measured forms a part of the walls of the sealed cell and the ac heater (conductive thin layer) 2 is ac joule-heated by a generator 40 of a modulated ac current such as a function synthesizer. In the sealed cell 30, a microphone 50 is installed air-tightly as a sound signal detector, and the output is amplified by a lock-in amplifier 60 to measure the ac component of the periodic sound wave in the sealed cell.

The lock-in amplifier 60 obtains a dc component from the product of the reference ac current from the ac current generator 40 and the detected wave. It has a selectivity so that noises other than necessary frequencies are almost completely eliminated.

The output signals of the lock-in amplifier 60 are sent to a data processor 70 (e.g., personal computer) to determine the thermal diffusivity. The calculation method of the thermal diffusivity is as follows.

Since the joule heat is maximized at the peak point regardless of the current being positive or negative, the cycle of the temperature oscillation is twice the cycle of the ac current. Accordingly, the ac component of the temperature of the ac heater 2 varies with a frequency f, assuming that the frequency of the modulated ac current is f/2. The varied temperature is expressed as $$T(t) = T_0 \cos(\omega t) \qquad (1)$$

taking angular frequency as $\omega(=2\pi f)$, as described above.

The heat energy is transmitted by thermal conduction, causing a periodic temperature oscillation in the gas in the sealed cell in contact with the opposite measurement surface and producing a periodic sound wave in agreement in phase with the temperature oscillation on the measurement surface of the sample. Taking the thickness of the measurement sample as d and the thermal diffusivity as $\alpha$, then the varied temperature is $$T(t) = T_0 \exp(-\sqrt{\omega/2\alpha d})\cos(\omega t - \sqrt{\omega/2\alpha d}). \qquad (2)$$

and noting only the phase shift between the temperature of ac heater and the temperature of opposite surface, it is $$\Delta\theta = \sqrt{\omega/2\alpha d} + \beta \qquad (3)$$

wherein $\Delta\theta$ and $\beta$ have the same meaning as already defined. The $\Delta\theta$ agrees with the phase shift of the formerly described periodic sound wave. Therefore, by introducing $\omega = 2\pi f$ in equation (3) followed by modification.

$$\Delta\theta = d\sqrt{\pi/\alpha}\sqrt{f} + \beta \qquad (4)$$

is obtained, as described above.

Accordingly, with regard to a sample plate having a known thickness d, the thermal diffusivity $\alpha$ can be obtained from equation (4) for at least two points in modulation frequency and measuring the phase shift $\Delta\theta$ between the ac heater and the periodic sound wave measured by the sound signal detector, thereby determining the thermal diffusivity from the gradient of the phase shift to the square root of the modulation frequency f.

The lower limit of the frequency range suitable for this measurement is the frequency at which the thermal diffusion length ($\mu_s = \sqrt{2\alpha/\omega}$) is not more than the thickness d of the measurement sample plate and the upper limit is in such a frequency range that the periodic sound wave amplitude is larger than noises, the frequency range hence being 0.01 to 1,000 Hz, preferably 0.1 to 700 Hz, more preferably 1 to 500 Hz where the sample is a high molecular film having a thickness of about 100 μm.

The present invention basically makes use of the phenomenon that the phase shift between the heating surface by ac joule-heating and the periodic sound wave in the sealed cell caused by the temperature oscillation of the opposite surface depends on the modulation frequency of the ac current flowing through the heating surface. The present invention determines the thermal diffusivity by forming a minute conductive thin layer on a minute sample plate, and applying ac current to the thin layer to generate ac joule-heat and measuring the temperature oscillation on the opposite surface by way of the periodic sound wave. Since the minute conductive thin layer is merely formed on the minute measurement sample plate, it is easy to heat or cool the measurement sample uniformly. In addition, the apparatus is also simple and small.

BRIEF DESCRIPTION OF THE DRAWINGS

FIG. 1 shows an example in which a conductive thin layer is formed on one surface of the plate, while in FIG. 1' conductive thin layers are formed on the both surfaces.

FIGS. 2 and 3 give examples in which temperature oscillation response is used as the oscillation response, while in FIG. 8, periodic sound wave is used.

In the drawing, numerals represent as follows:
1—measurement sample plate
2—ac heater (electrically conductive thin layer)
3—resistance thermometer (electrically conductive thin layer)
4 & 40—ac current generator (function synthesizer)
5—dc source (battery)
6—resistance for preventing self heating
7 & 60—lock-in amplifier
8 & 70—data processor
9—heating and cooling cell for measurement sample plate 10—temperature controller
Δθ—phase shift
50—microphone
  f—frequency of temperature oscillation on temperature measuring surface
  T—measured temperature
  α—thermal diffusivity
  λ—thermal conductivity Preferred embodiments of the present invention will be illustrated with reference to the following examples.

EXAMPLE 1

In this example, the apparatus shown in FIG. 2 was used for the measurement.

As the measurement sample plate, there are used (1) a sapphire plate with a thickness of 98 μm and a size of 15 mm × 15 mm, masked with a polyester film of 0 mm × 3 mm on both sides in such a way that the ac heater side has a thickness of 500 angstroms of gold layer and the resistance thermometer side has a thickness of 800 angstroms of gold layer sputtered with gold onto the both sides, (2) and a polystyrene film with a thickness of 120 μm and a size of 15 mm × 10 mm, masked with a polyester film of 10 mm × 3 mm on both sides in such a way that the ac heater side has a thickness of 500 angstroms of gold layer and the resistance thermometer side has a thickness of 800 angstroms of gold layer sputtered with gold onto the both sides as is the case with the sapphire.

Figure 5:
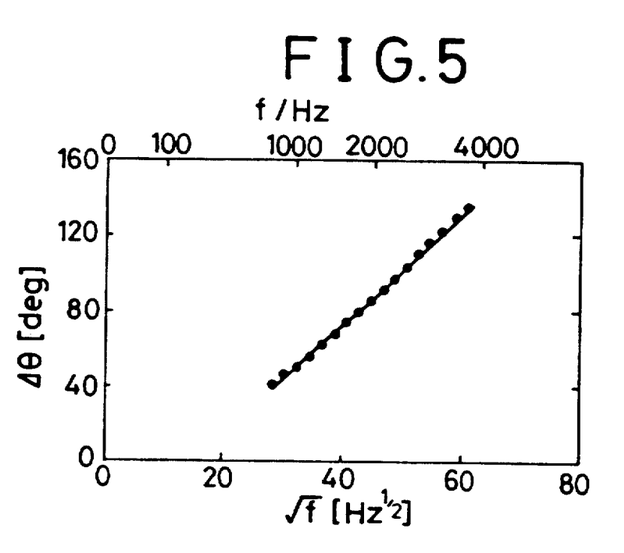
FIG. 5 gives a measurement example of the variation of the phase shift of the outputs between the ac heater and the ac component of the resistance thermometer with the square root of the frequency in the case of a sapphire plate.

FIG. 5 illustrates the variation of the phase shift between the ac heater and the outputs of ac component of the resistance thermometer with the square root of the frequency in the case of the sapphire plate. From the gradient obtained in the drawing, the thermal diffusivity is determined using the equation described earlier. In this measuring method, the use of a lock-in amplifier permits an almost complete elimination of noises other than necessary frequencies, and the measurement based on the phase shift produces no measurement errors due to the absolute value of temperature. Thus, measurement data excellent in accuracy and reproducibility can be obtained. The thermal diffusivity determined from the gradient is approximately $1.2 \times 10^{-5}$ m²/sec and agrees well with the values of the thermal diffusivity of sapphire given in literatures and the calculated values of the thermal diffusivity from other thermal properties.

Figure 6:
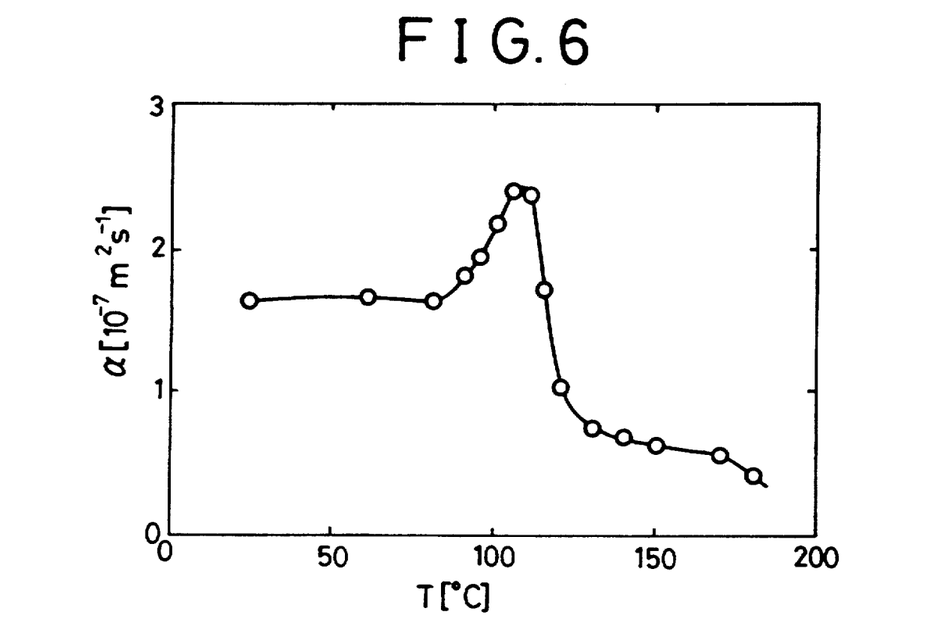
FIG. 6 shows a measurement example of the temperature dependence of the thermal diffusivity measured with a polystyrene film.

FIG. 6 shows the results of measurement on the temperature dependence of the thermal diffusivity of the polystyrene film. The glass transition temperature of this measurement sample plate is about 105° C., but as shown in the drawing, the thermal diffusivity can be measured in the wide range of temperature above the glass transition temperature. Further, such interesting results are obtained that the thermal diffusivity has a peak in the vicinity of the glass transition temperature, and a larger difference is observed also between the thermal diffusivities in the liquid and solid states.

Thus, the present invention permits studying minutely the variation of the thermal diffusivity due to the morphological changes and molecular motion of a substance and performing precise product designs, etc. at high temperatures which have been difficult to evaluate to date. Further, the present invention makes it possible to perform a more accurate analysis at actual processing and use temperatures in the utilization of various simulation programs.

Figure 7:
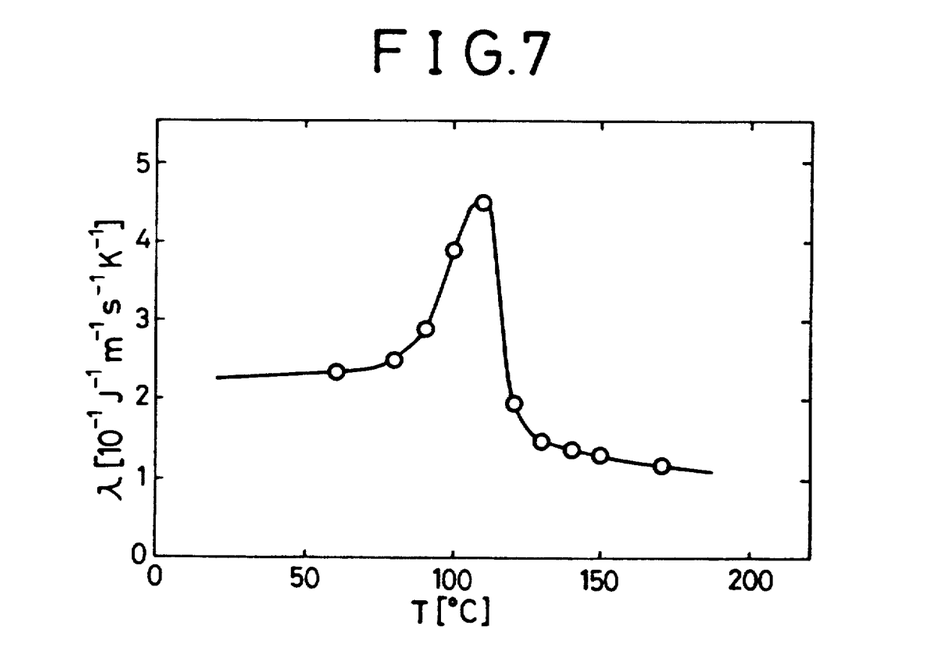
FIG. 7 is a drawing illustrating an example of the temperature dependence of the thermal conductivity determined by using the measured value of the thermal diffusivity and the measured values of the specific heat and density obtained by other methods in the case of the polystyrene film.

FIG. 7 shows the results of measurement of the temperature dependence of the thermal conductivity determined from the measured value of the thermal diffusivity obtained by the method of the present invention and those of the specific heat and density obtained by other methods in the case of the polystyrene film. The specific heat was measured by a differential scanning calorimeter while the density by a capillary-type P-V-T measuring instrument. The thermal conductivity thus obtained has a peak in the vicinity of the glass transition temperature as in the case of the thermal diffusivity, and its whole behavior is also similar to that of the thermal diffusivity. The thermal diffusivity contributes to the thermal conductivity more than the specific heat and density. Using the results, it is possible to perform precisely the product design, etc. at high temperatures which has been difficult to evaluate to date. Further, an accurate analysis at actual processing and use temperatures can be made in the utilization of various simulation programs.

Further, similar measurements have been attempted with the apparatus shown in FIG. 3 and it was confirmed to obtain substantially the same results.

EXAMPLE 2

The apparatus shown in FIG. 8 was used. As the measurement sample was used a PET (polyethylene terephthalate) film of a thickness of 100 μm and a size of 10 mm × 10 mm, having 300 angstroms of gold vapor-deposited layer by sputtering as the ac heater.

Figure 9:
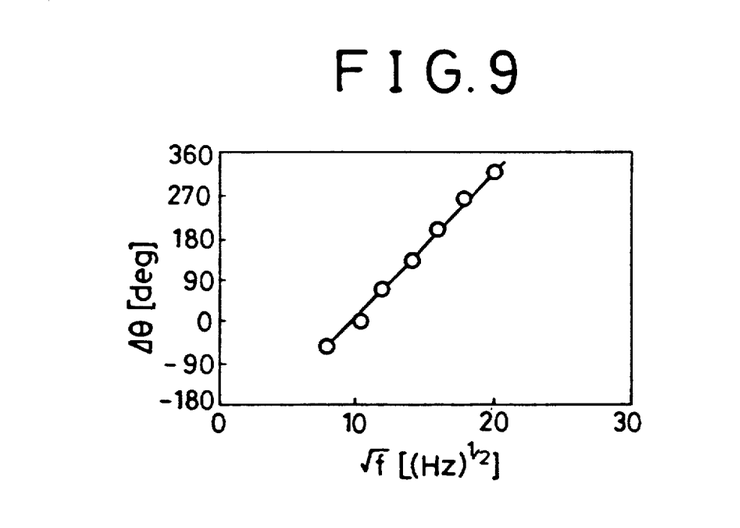
FIG. 9 is a drawing illustrating a measurement example of the variation of the phase shift between the ac heater and the outputs of sound signal detector with the square root of the frequency measured with a PET (polyethylene terephthalate) film.

FIG. 9 shows the variation of the phase shift of the ac heater and the outputs of sound signal detector with the square root of the modulation frequency measured with said measurement sample. Using the gradient obtained in this drawing, the thermal diffusivity was obtained in the same manner using the equations described above.

Industrial Applicability

As has been described above, the following effects can be obtained according to the present invention, which are suitably applicable to such areas as the development, product design, and analysis by simulation of a variety of materials including high molecular materials (polymers), ceramics, etc.

(1) Since the measurement sample plate is of a very small amount (and thin thickness) and the conductive thin layers are completely adhered to the plate so as to measure only the phase shift of the ac components of temperature, the absolute value of temperature has no significance, so that accurate measurements with little errors can be obtained and miniaturization of the apparatus and speed-up of the measurement can be realized. Consequently, various problems involved in the conventional Angstrom method,—that is, a large amount of sample required, a large adiabatic equipment for minimizing heat loss, a relatively long time required for measurement, and limited measuring objects to materials of relatively large thermal diffusivities, can be entirely eliminated.

(2) Since the conductive thin layers are formed by completely adhering to the sample plate by sputtering, etc. and are so thin that the contacting interface can be ignored, there is raised no problem of heat loss.

Therefore, heating irregularities and heat loss errors can be prevented, which occurs in the flash method and PAS method utilizing light absorption. Further, a sound signal detectory used in the PAS method is not necessary in this invention, there is no error caused by vibration and noises.

(3) The sample is so microminiaturized and the apparatus is so simplified and miniaturized that it is easy to change the measurement atmosphere temperature by heating or cooling the cell equipped with the sample and thereby to measure the temperature dependence of the thermal diffusivity.

Where the use and processing conditions of an actual product are examined and its analysis based on actual phenomena is carried out, it is necessary to know its thermal properties in the wide range of temperature from room temperature to the melting temperature or above. However, according to the present invention, it is possible to measure the thermal characteristics of a sample from many sides without making the apparatus complicated and enlarged due to the bulk treatment of samples or providing air-tighted cell as is the case with the conventional methods and hence to cope flexibly with the recent diversified studies and developments of material characteristics.

(4) The thermal conductivity can be obtained from the measured value according to the present invention and the specific heat and density obtained by other methods.

When the characteristics of a material are studied and developed in due consideration of the properties involved in the heat transfer of the material, it is important to know not only its thermal diffusivity but also its thermal conductivity. According to the present invention, however, it is possible to carry out a diversified study and development of the characteristics of the material by the use of both of the thermal diffusivity and the thermal conductivity.

What is claimed is:

1. A method for measuring the thermal diffusivity in the thickness direction of a thin sample plate of relatively non-conductive material which comprises the steps of:

forming a conductive thin layer on at least one surface of said thin sample plate to allow the thin layer to function as an ac heater generating joule heat;

applying an ac current modulated with a given modulation frequency to the ac heater so as to produce ac joule-heating;

generating an oscillation response corresponding to said ac joule-heating on the opposite surface of the ac heater; and measuring the phase shift between said oscillation response and the ac joule-heating, thereby obtaining the thermal diffusivity in the thickness direction of said sample plate.

2. The method of measuring the thermal diffusivity of the sample plate according to claim 1 wherein the oscillation response is a temperature oscillation response.

3. The method for measuring the thermal diffusivity according to claim 2 which comprises the steps of:

forming a conductive thin layer on both surfaces of the thin sample plate to allow one of the thin layers to function as the ac heater generating joule heat and to allow the other thin layer to function as a resistance thermometer making use of the variation of the resistance with temperature;

the step of generating an oscillation response including generating a temperature oscillation response corresponding to said ac joule-heating in said resistance thermometer; and the step of measuring the phase shift including measuring the phase shift between the temperature oscillation response and the ac joule heating for at least two points in said modulation frequency range, thereby obtaining the thermal diffusivity in the thickness direction of said sample plate from the relationship between the phases shifts and said modulation frequency.

4. The method for measuring thermal diffusivity according to claim 3 wherein the sample plate is a plate fabricated from relatively non-conductive material selected from high molecular materials (polymers), organic dyestuff, mineral ores, glasses and ceramics.

5. The method for measuring thermal diffusivity according to claim 3 wherein the thin layers functioning as the ac heater and the resistance thermometer are formed by sputtering.

6. The method for measuring thermal diffusivity according to claim 3 wherein the temperature dependence of the thermal diffusivity is measured at desired temperatures by heating or cooling the sample.

7. A method for measuring thermal conductivity of a thin sample plate comprising measuring the thermal diffusivity of the sample plate according to the method described in claim 7 and obtaining thermal conductivity using a specific heat and density of said sample plate.

8. An apparatus for measuring thermal diffusivity in the thickness direction of a thin sample plate provided with conductive thin layers on both surfaces which comprises:

an ac current generation means for applying an ac current with a given amplitude of modulation to one of the conductive thin layers;

a dc current supplying means for applying a given dc current to the other conductive thin film which is temperature dependent; and a lock-in amplifier for amplifying a voltage which varies in accordance with changes in resistance of said temperature dependent conductive thin layer.

9. The apparatus for measuring thermal diffusivity according to claim 8 which further comprises a cell for accommodating the thin sample plate.

10. The apparatus for measuring thermal diffusivity according to claim 9 which further comprises a means for heating or cooling the sample in the cell, thereby giving the temperature dependence of the thermal diffusivity by changing the measurement atmosphere temperature.

11. The method for measuring thermal diffusivity according to claim 2 which comprises:

providing a cell equipped with a sound signal detector;

incorporating said sample plate which has the conductive thin layer functioning as the ac heater on the one surface and which has an opposite surface that serves as the measurement surface, into said cell in such a way that the measurement surface constitutes a part of the inner walls of said cell;

said step of generating an oscillation response including generating a temperature oscillation response corresponding to said ac joule-heating on said measurement surface, thereby inducing a periodic sound wave; and said step of measuring the phase shift including measuring the phase shift between the ac joule heating and the periodic sound wave with a sound signal detector for at least two points in said modulation frequency range, thereby obtaining the thermal diffusivity in the thickness direction of the sample plate from the relationship between the phase shifts and said modulation frequency.

12. The method for measuring thermal diffusivity according to claim 12 wherein the sample plate is a plate fabricated from a relatively non-conductive material selected from high molecular compounds (polymers), organic dyestuffs, mineral ores, glasses and ceramics.

13. The method for measuring thermal diffusivity according to claim 11 wherein the thin layer functioning as the ac heater is formed by sputtering.

14. The method for measuring thermal diffusivity according to claim 12 wherein the thermal diffusivity is temperature dependent, the temperature dependence of the thermal diffusivity being measured at desired temperatures by heating or cooling the sample.

15. A method for measuring thermal conductivity of a thin sample plate comprising measuring the thermal diffusivity of the sample plate according to the method described in claim 14 and obtaining thermal conductivity using the specific heat and density of said sample plate.

16. An apparatus for measuring thermal diffusivity in the thickness direction of a thin sample plate, on one surface of which is formed a conductive thin layer functioning as an ac heater and an opposite surface of which serves as a measurement surface, which comprises:
   an ac current generation means for applying an ac current with a given amplitude of modulation to the conductive thin layer;
   a cell having a sound signal detector in an interior thereof which outputs output signals, said cell having inner walls and being capable of incorporating the sample plate in such a way that the measurement surface of said sample plate comprises a part of the inner walls of the cell; and
   a lock-in amplifier for amplifying the output signals of said sound signal detector.

17. The apparatus for measuring thermal diffusivity according to claim 16 which further comprises a means for heating or cooling the sample in the cell to change a measurement atmosphere temperature in the cell so that a temperature dependence on the thermal diffusivity can be measured.

18. A method for measuring thermal conductivity of a thin sample plate comprising measuring the thermal diffusivity of the sample plate according to the method described in claim 3 and obtaining thermal conductivity using a specific heat and density of said sample plate.

19. A method for measuring thermal conductivity of a thin sample plate comprising measuring the thermal diffusivity of the sample plate according to the method described in claim 4 and obtaining thermal conductivity using a specific heat and density of said sample plate.

20. A method for measuring thermal conductivity of a thin sample plate comprising measuring the thermal diffusivity of the sample plate according to the method described in claim 5 and obtaining thermal conductivity using a specific heat and density of said sample plate.

21. A method of measuring thermal conductivity of a thin sample plate comprising measuring the thermal diffusivity of the sample plate according to the method described in claim 11 and obtaining thermal conductivity using a specific heat and density of said measurement sample.

22. A method for measuring thermal conductivity of a thin sample plate comprising measuring the thermal diffusivity of the sample plate according to the method described in claim 12 and obtaining thermal conductivity using a specific heat and density of said measurement sample.

23. A method for measuring thermal conductivity of a thin sample plate comprising measuring the thermal diffusivity of the sample plate according to the method described in claim 13 and 24. The method for measuring thermal diffusivity according to claim 3, wherein the thin layers functioning as the ac heater and the resistance thermometer are formed by vapor deposition.

25. The method for measuring thermal diffusivity according to claim 3, wherein the thin layers functioning as the ac heater and the resistance thermometer are formed by coating.

26. The method for measuring thermal diffusivity according to claim 3, wherein the thin layers functioning as the ac heater and the resistance thermometer are formed by adhesion.

27. The method for measuring thermal diffusivity according to claim 3, wherein the thin layers functioning as the ac heater and the resistance thermometer are formed by applying pressure.

28. The method for measuring thermal diffusivity according to claim 12, wherein the thin layers functioning as the ac heater is formed by adhesion.

29. The method for measuring thermal diffusivity according to claim 11, wherein the thin layer functioning as the ac heater is formed by vapor deposition.

30. The method for measuring thermal diffusivity according to claim 11, wherein the thin layer functioning as the ac heater is formed by coating.

31. The method for measuring thermal diffusivity according to claim 11, wherein the thin layer functioning as the ac heater is formed by applying pressure.

32. The method of measuring the thermal diffusivity of a sample plate according to claim 1, wherein the oscillation response is a periodic sound wave.

* * * * *

UNITED STATES PATENT AND TRADEMARK OFFICE
CERTIFICATE OF CORRECTION

PATENT NO. : 5,080,495
DATED : January 14, 1992
INVENTOR(S) : Hashimoto et al

It is certified that error appears in the above-indentified patent and that said Letters Patent is hereby corrected as shown below:

In column 16, line 21, after "and" insert --obtaining thermal conductivity using a specific heat and density of said measurement sample.--

In column 16, line 39, delete "12 and insert therefor --11--.

Signed and Sealed this

Seventh Day of December, 1993

Attest:

BRUCE LEHMAN

*Attesting Officer*   *Commissioner of Patents and Trademarks*